US006069302A

United States Patent [19]
Osborn et al.

[11] Patent Number: 6,069,302
[45] Date of Patent: May 30, 2000

[54] HYBRID SPRING OILSEED *BRASSICA NAPUS* WITH WINTER GERMPLASM INTROGRESSION

[75] Inventors: Thomas C. Osborn; David V. Butruille, both of Madison, Wis.

[73] Assignee: Wisconsin Alumni Research Foundation, Madison, Wis.

[21] Appl. No.: 08/928,799

[22] Filed: Sep. 12, 1997

Related U.S. Application Data

[60] Provisional application No. 60/026,086, Sep. 13, 1996.

[51] Int. Cl.$^7$ .............................. A01H 5/00; A01H 5/10; A01H 1/04
[52] U.S. Cl. ......................... 800/306; 800/260; 800/266; 800/267; 800/298
[58] Field of Search .................................... 800/260, 266, 800/267, 276, 298, 306; 435/6

[56] References Cited

U.S. PATENT DOCUMENTS

| | | |
|---|---|---|
| 5,385,835 | 1/1995 | Helentjaris et al. . |
| 5,476,524 | 12/1995 | Leon et al. . |
| 5,492,547 | 2/1996 | Johnson . |
| 5,574,210 | 11/1996 | Saghai-Maroof et al. . |

OTHER PUBLICATIONS

Butruille, D.V., et al., "Effect of winter germplasm introgression on hybrid performance of spring rapeseed," *Agronomy Abstracts* (1995 Annual Meetings of Am. Soc. Agron., Crop Sci. Soc. Am., Soil Sci. Soc. Am.), p. 173 (abstract mailed Sep. 13, 1995).

Butruille, D.V., et al., Poster session presented at 1995 Annual Meetings of Am. Soc. Agron., Crop Sci. Soc. Am., Soil Sci. Soc. Am.; St. Louis, MO; Oct. 29–Nov. 3, 1995.

Butruille, D.V., et al., "Hybrid Performance of Spring Oilseed Rape with Winter Germplasm Introgression," abstract submitted to *Agronomy Abstracts* for 1996 Annual Meetings of Am. Soc. Agron., Crop Sci. Soc. Am., Soil Sci. Soc. Am.; meeting held Nov. 1996.

Diers, B.W., et al., Relationship between Heterosis and Genetic Distance Based on Restriction Fragment Length Polymorphism Markers in Oilseed Rape (*Brassica napus* L.), *Crop Science*, 36(1):79–83 (1996).

Diers, B.W., et al., "Genetic diversity of oilseed *Brassica napus* germ plasm based on restriction fragment length polymorphisms," *Theor. Appl. Genet.*, 88:662–668 (1994).

Ferreira, M.E., et al., RFLP mapping of *Brassica napus* using doubled haploid lines, *Theor. Appl. Genet.*, 89:615–621 (1994).

Ferreira, M.E., et al., "Mapping loci controlling vernalization requirement and flowering time in *Brassica napus*," *Theor. Appl. Genet.*, 90:727–732 (1995).

Thormann, C.E., et al., "Mapping loci controlling the concentrations of erucic and linolenic acids in seed oil of *Brassica napus* L.," *Theor. Appl. Genet.*, 93:282–286 (1996).

Toroser, D., et al., RFLP mapping of quantitative trait loci controlling seed aliphatic–glucosinolate content in oilseed rape (*Brassica napus* L.), *Theor. Appl. Genet.*, 91:802–808 (1995).

Johnston, T.D., "A Comparison of Inbred Lines and their $F_1$ Hybrids in Forage Rape (*Brassica napus* L.)," *Euphytica* 20:81–85 (1971).

*Primary Examiner*—Gary Benzion
*Assistant Examiner*—Melissa L. Kimball
*Attorney, Agent, or Firm*—Rothwell, Figg, Ernst & Kurz

[57] ABSTRACT

A method for obtaining hybrid *Brassica napus* having high-parent heterosis with respect to seed yield includes the steps of crossing a spring line to a (winter×spring) $F_1$ hybrid, where the (winter×spring) $F_1$ hybrid retains a spring growth habit.

18 Claims, 3 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 406 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Brassica napus (vii) IMMEDIATE SOURCE:
      (B) CLONE: WG6B10.R24

(ix) FEATURE:
     (A) NAME/KEY: primer_bind
     (B) LOCATION: 186..205

(xi) SEQUENCE DESCRIPTION: SEQ ID NO:1:

```
AATAAAGGGA ACAAAAGCTG GAGCTCCACC GCGGTGGCGG CCGCTCTAGA ACTAGTGGAT    60

CCCCCGGGCT GCAGCAACAA CCATGAATCT ATTGCATACG ATGAAACATC AGCCCAGAAA   120

ATGAGATTGG ATCCTTAAAT GGACGATAGC CCGGGCTACA TCCAACCTCA GGGTGTTGCA   180

ATCGAGAATC CACTAACCCA CCAGCTCGGT TTCTGAAGTC GATAAGTTCA TCGAAAAAAC   240

ACAGAAGTGT CGTTTACAGA TCGCATCGTC ACGCTCTCAT CCCAAACATC AAACTAAAAA   300

TCTCTTCATA CGATGGGAAA ACCTACACTT TGTAAAGAAA CTATGGTAAG ACTTGATCCC   360

ATTTAGGATA TGTAGGCAAC CCAATAAATA TAGTATTAAT TAAAAT              406
```

(2) INFORMATION FOR SEQ ID NO:2:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Brassica napus (vii) IMMEDIATE SOURCE:
        (B) CLONE: WG6B10.T7

(ix) FEATURE:
        (A) NAME/KEY: primer_bind
        (B) LOCATION: 146..165

(xi) SEQUENCE DESCRIPTION: SEQ ID NO:2:

```
GGGTACCGGG CCCCCCCTCG AGGTCGACGG CATCGATAAG CTTGATATCG AATTCCTGCA    60

GTCTCATTCT ACATGTGAAC GTCCGTTTCG TAGCAAAGGC TTCTCCTTCA TCACCAGCCA   120

CACACTCATC TTACTACAAC ACTTGTCCTT CCCAATCACC AAATCTCTGT ACGAACCATT   180

CGTCCAAACG ACTCTCCCTA AACCGTCCGA TATAAAACCA GGACACGTGT CCCTCTCCAG   240

ATTCATCTTC TTTTCCTCGT CCGAACACCC TAACTCGTAC TCCCCCTCCG TTACGCACTC   300

TACCGTTAAC AGCGACGACA CAACCGTTTC CGTTCTCGCG TTAGTAATCC CTCCGGCAGA   360

TCTAAACTCT TCTTCGGCGC TTGATAACGT CCGTCATCTC CGAAACTCAA CCACGAAGGA   420

CGCCGGCGAG GCAACAAAAA CCCTAGGGGG GTTCCTTCCT CCTCTCAGGA GTCT        474
```

(2) INFORMATION FOR SEQ ID NO:3:

(i) SEQUENCE CHARACTERISTICS:
        (A) LENGTH: 513 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Brassica napus (vii) IMMEDIATE SOURCE:
        (B) CLONE: WG7B3.R24

```
        (ix) FEATURE:
              (A) NAME/KEY: primer_bind
              (B) LOCATION: 93..112

(xi) SEQUENCE DESCRIPTION: SEQ ID NO:3:

GCCAAGCTCG AAATTAACCC TCACTAAAGG GAACAAAAGC TGGAGCTCCA CCGCGGTGGC      60

GGCCGCTCTA GAACTAGTGG ATCCCCCGGG CTGCAGCAGG ATACGCAGTA ACTCCCAGCA     120

CCGTCTCTAT GTTCTTCTTC ACATCAGCAA CCTGATCACA CTCGCATATA TATTTTTTGT     180

ATATAACCAT CAGTTAAATC AGCTACTTCA CGAAAACGGA ACAATATCAA TACAGAGGAG     240

ACGCATGGAT CTAAGAAACG AAACCCTACA AGCATCTTTG CGTATCACTT TCAGAGTTCA     300

TATTGACGAA AGAGAACATG ATTCAAAGAC TCTAGAGTAT TACTCTCTAT AGAAACCACC     360

AAAAGTAACT AACTTGCCGA TCAAGAAAGA GTGATCAATA TGCTACCGTA GTGAACAAGA     420

AATAGAACGA AAGATATGAA ACGCAACTGT GAAGTTACGT ACCGAATCCT CGGGTTTGAC     480

TTGGATCTTC GAACCGAGCT CCCTTCAGAG TTT                                 513

(2) INFORMATION FOR SEQ ID NO:4:

(i) SEQUENCE CHARACTERISTICS:
              (A) LENGTH: 516 base pairs
              (B) TYPE: nucleic acid
              (C) STRANDEDNESS: double
              (D) TOPOLOGY: linear (ii) MOLECULE TYPE: DNA (genomic)

(vi) ORIGINAL SOURCE:
              (A) ORGANISM: Brassica napus (vii) IMMEDIATE SOURCE:
              (B) CLONE: WG7B3.T7

(ix) FEATURE:
              (A) NAME/KEY: primer_bind
              (B) LOCATION: 358..377

(xi) SEQUENCE DESCRIPTION: SEQ ID NO:4:

GGTACCGGGC CCCCCCTCGA GGTCGACGGT ATCGATAAGC TTGATATCGA ATTCCTGCAG      60

GAAATTCTGG AAGTGATAGA GGAACACAAT CCGCAATTGG TTCAGTTTAT TCTAGACAAC     120

AAAGCAGACT TCTTACGCTT AGTACTGGAC CAGCCTCAGG AACACCAAGA CGACGACGTC     180

TTACACTTTC AAAGCAACGA ACCAAACAAC GGAGGAGAAA GGTACTGAAC TTAATTATCA     240

TAATGTTAGT AGTAAAATGA TATAGAAATT AACTGAGATT TTCTTGTGGA TTCTTTGTTG     300

TTGTGTGATT CAGTGGAAAC CAAGTGGGAA AGTCTGAAGA AACCGAAGTT GAGCAGCCTC     360

AAGCAGACCA AACCAACAAA CCAAACAACG GAGATGGGTA CAAAAATTTA CCATAAGTAG     420

TGTTAGTAGT AAAATAATGC AGAAATTAAC TGCGCTTTCT TGTGGATTCT TTGTTGTGTG     480

TGATTCAGTG ACAACCAGTG GGAGGAGAGT CTGAGG                              516
```

HYBRID SPRING OILSEED BRASSICA NAPUS WITH WINTER GERMPLASM INTROGRESSION

CROSS-REFERENCE TO RELATED APPLICATIONS

This application claims the benefit of U.S. Provisional Patent Application Number 60/026,086, filed Sep. 13, 1996.

STATEMENT REGARDING FEDERALLY SPONSORED RESEARCH OR DEVELOPMENT

This invention was made with United States government support awarded by the following agencies: USDA Award Nos: 58-1908-0-117; 59-319R-4-027; 94-37300-0326; 91-37301-6597; Hatch Nos: 3382-0382; and Award No: AGR 593-0213-01. The United States has certain rights in this invention.

BACKGROUND OF THE INVENTION

The present invention relates generally to genetic procedures involving oilseed Brassica napus plants and relates more particularly to procedures intended to increase yield potential of oilseed hybrids having a growth habit of a spring line, by introgression of winter germplasm.

Brassica napus is the most productive oilseed rape. Edible oilseed rape ("canola") is a desirable edible oil produced by certain B. napus which contains less than 2% erucic acid in the oil and less than 30 micromoles of oil-extracted aliphatic glucosinolates per gram of air-dried meal. Canola oil has the lowest percentage concentration of saturated fatty acids of commonly used vegetable oils. Other B. napus produces inedible oils having utility as an industrial lubricant.

Phylogenetic restriction fragment length polymorphism ("RFLP") analyses have differentiated the germplasm of oilseed B. napus into two main groups: winter lines (used in most of Europe) and spring lines (used mostly in northern Europe and Canada). A third, intermediate, category includes East Asian and Australian genotypes that have both growth habits. Diers, B. W. and T. C. Osborn, "Genetic Diversity of Oilseed Brassica napus Germplasm Based on Restriction Fragment Length Polymorphisms," Theor. Appl. Genet. 88:662–668 (1994), incorporated herein by reference.

Winter lines are generally recognized as producing higher seed yields than spring lines. However, in northern latitudes, typified by the northern tier United States and Canada, existing winter lines are not sufficiently hardy to endure overwintering. Thus, only lower-yielding spring lines can grow. Typical spring lines now grown in Canada have an average yield of approximately 1300 kg/ha, whereas yields of 3000 kg/ha are realized in countries that grow essentially all winter rapeseed. Despite these low yields, the spring lines are acceptable in Canada and in the very northern tier United States, insofar as the short growing season and harsh winter do not allow for high yields of any crop. To be economically viable throughout more of the northern tier states, oilseed B. napus lines should yield at least about 2,325 kg/ha or 2000 lb/acre. See Oplinger, E. S. et al., Alternative Field Crops Manual-Canola (Rapeseed) (1989).

Spring/winter growth habit in B. napus appears to be under oligogenic control. Thurling, N. and L. D. Vijendra Das, "Genetic Control of Pre-Anthesis Development of Spring Rape (Brassica napus L.). II. Identification of Individual Genes Controlling Developmental Pattern," Aust. J. of Agric. Res. 30:261–271 (1979); Van Deynze, R. and K. P. Pauls, "The Inheritance of Seed Colour and Vernalization Requirement in Brassica napus Using Doubled Haploid Populations," Euphytica 74:77–83 (1994).

B. napus hybrids are known to exhibit heterosis or hybrid vigor. Sernyk, J. L. and B. R. Stefansson, "Heterosis in Summer Rape (Brassica napus L.)", Can. J. Plant Sci. 63:407–413 (1983); Grant, I. and W. Beversdorf, "Heterosis and Combining Ability Estimates in Spring-Planted Oilseed Rape (Brassica napus L.)," Can. J. of Genet Cytol., 27:472–478 (1985); Lefort-Buson et al., "Heterosis and Genetic Distance in Rapeseed (Brassica napus L.): Crosses Between European and Asiatic Selfed Lines," Genome 29:413–418 (1987); Brandle, J. E. and P. B. E. McVetty, "Heterosis and Combining Ability in Hybrids Derived from Oilseed Rape Cultivars and Inbred Lines," Crop Sci. 29:1191–1195 (1989). Among spring cultivars, higher heterosis levels are observed in offspring of distantly related crosses, such as a cross between the Canadian spring cultivar Regent and the Australian spring cultivar Marnoo (Brandle and McVetty, supra; Diers, et al., "Relationship Between Heterosis and Genetic Distance Based on Restriction Fragment Length Polymorphism Markers in Oilseed Rape (Brassica napus)," Crop Sci. 36:79–83 (1996).

Notably, spring and winter growth habits can be distinguished from one another by RFLPs linked to distinct vernalization-responsive flowering time loci. Ferreira, M. E., et al., "Mapping Loci Controlling Vernalization Requirement and Flowering Time in Brassica napus," Theor. Appl. Genet. 98:727–732 (1995); see also Osborn, T. C. et al, "Comparison of Flowering Time Genes in Brassica rapa, B. napus, and Arabadopsis thaliana," Genetics 146:1123–1129 (1997). A major vernalization-responsive flowering time locus (vfn1; formerly vn1) was mapped as a quantitative trait locus ("QTL") of Linkage Group (LG) 9 using RFLP markers in a doubled haploid population derived from the cross of a European winter cultivar (Major) and a Canadian spring cultivar (Stellar). Vernalization appears to have great influence on the effect of this major gene. In the same doubled haploid population, a second vernalization-responsive flowering time locus (vfn2; formerly vn2) was RFLP-mapped as a QTL of LG12, and a third such gene (vfn3; formerly vn3) was mapped to LG16. The vfn3 gene appears to be less critical to flowering time. The locations of these genes were determined using Mapmaker-QTL.

What is desired is an oilseed B. napus line having a spring growth habit and higher seed yield potentials than other lines that can grow in an environment that supports lines having spring growth habit. Such a hybrid would provide farmers with additional market options and new choices for crop rotation.

The papers noted in this Background are incorporated herein by reference.

BRIEF SUMMARY OF THE INVENTION

The present invention is summarized in that a method for producing a desired high yield oilseed B. napus hybrid includes the step of crossing an oilseed B. napus that has the growth habit of a spring line, but which contains germplasm derived from a winter line, to spring tester lines that represent a range of genetic diversity. Then, hybrids having suitably high yield are selected for further breeding or for commercial use. Winter-type B. napus is genetically very different from spring types and represents an untapped resource of genetic diversity for spring type plants, to broaden the genetic base and to increase hybrid yields. Introgression typically requires a lengthy procedure of backcrossing and testing to identify spring-type lines that have acquired favorable genes from winter types.

The winter germplasm can be combined with the spring growth habit in several ways. In a first approach, the oilseed *B. napus* that has the growth habit of a spring line, but which contains germplasm derived from a winter line, is obtained from microspore-culture and colchicine treatment to create doubled haploid lines from the $F_1$ of a winter line and a spring line.

In a second approach, an oilseed *B. napus* having the desired properties is obtained by repeatedly backcrossing winter germplasm into the F1 progeny of a winter line and a spring line, followed by repeated selfing of the backcross progeny. This approach can result in lines having spring growth habit but with more winter germplasm on average than those obtained in the first approach.

In a third approach, the desired oilseed *B. napus* is obtained by repeatedly backcrossing spring germplasm into the F1 progeny of a winter line and a spring line, followed by repeated selfing of the backcross progeny. This approach produces a higher frequency of lines with spring growth habit and the derived populations can be used directly obtain mapping information about loci from the winter parent important to high yield.

The resulting progeny of each approach, which can be used subsequently as a parent in the above-noted cross with the spring line, can have a spring growth habit and certain winter germplasm that correlates with high seed yield. The progeny most suitable for use in hybrid formation can be selected in test crosses against spring testers that represent a range of genetic diversity among spring lines.

It is an object of the present invention to introduce winter germplasm into spring oilseed *B. napus* to improve the seed yield of hybrid oilseed *B. napus* having a spring-type growth habit.

It is a feature of the present invention that spring lines having winter germplasm introgression can demonstrate higher yields, on average, when crossed to spring tester lines than are observed either in other (spring×spring) hybrid crosses or in open pollination. Some individual lines show markedly higher yields than is observed in (spring×spring) hybrid crosses or in open pollination.

It is an advantage of the present invention that introduction of winter germplasm into spring lines can further enhance hybrid vigor in crosses between distantly related lines having spring growth habit.

Other objects, features, and advantages of the present invention will become apparent upon consideration of the following detailed description, taken in conjunction with the accompanying drawings.

DETAILED DESCRIPTION OF THE INVENTION

Figure 1:
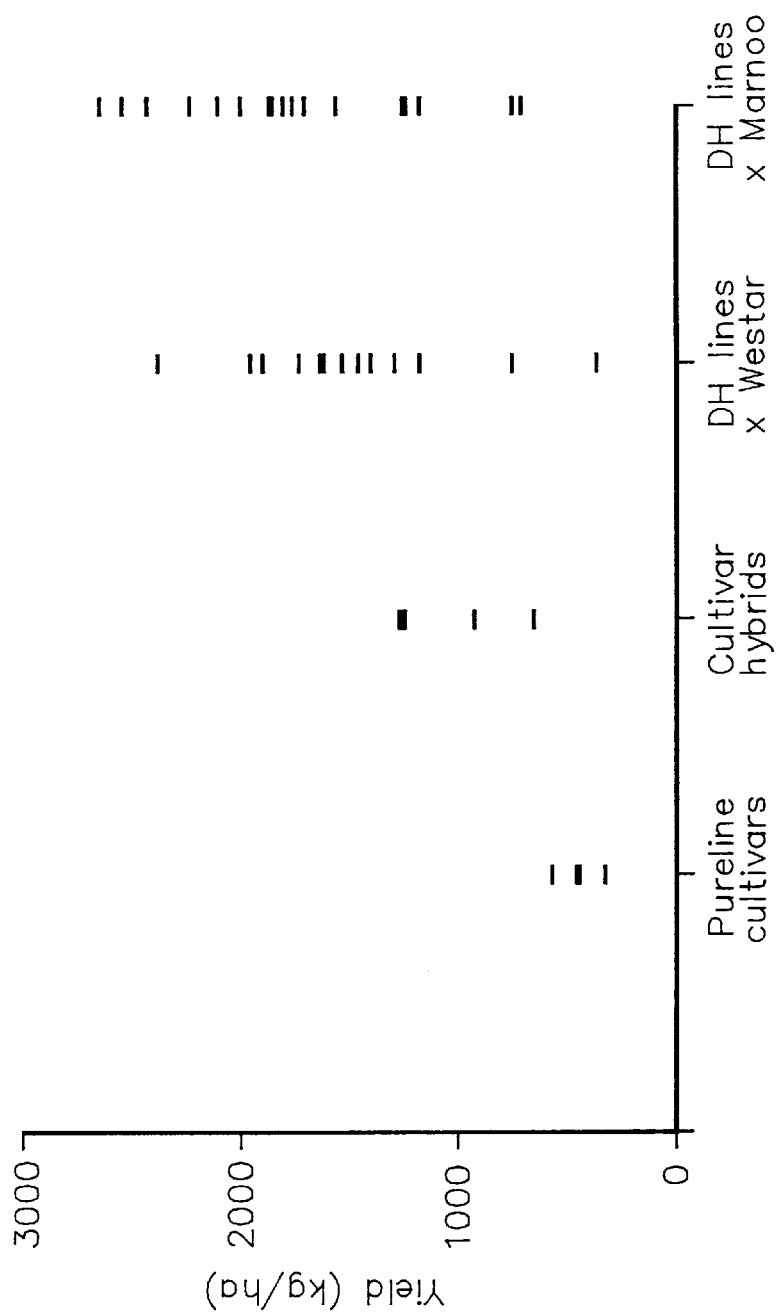
FIG. 1 shows the average yields of the entries in the first test, categorized by type of germplasm. DH lines are doubled-haploids that contain winter germplasm.

The systems described here are intended to allow plant breeders to make and reliably reproduce spring oilseed rape (*Brassica napus*) with winter germplasm introgression. Products of these breeding systems can be readily used to create hybrids with spring rape or canola, which hybrids demonstrate heterosis vigor (or "hybrid vigor") that results in higher seed yields than are observed using pure line cultivars or hybrids between spring cultivars. Increased yield is characterized in these hybrids as statistically significant increases in yield (at 5% probability) over the yield of cultivars compared in a replicated trial. A suitable hybrid produced according to the present invention has a seed yield reproducibly higher in more than one growing season than hybrids derived only from spring lines.

In this patent application, a "line" is a maintained genetic stock of *Brassica napus* having the desired growth habit (winter or spring). A "line" can be a cultivar or open pollinated stock, now existing or in the future developed, or a derivative of a cultivar or open pollinated stock, including but not limited to a hybrid and a line obtained by microspore culture and colchicine doubling (a "doubled-haploid"), which is selected by a method now known or in the future developed, or the like. It is noted that a product of the method of the present invention can be used as a starting material in another application of the method.

A spring growth habit line (or "annual") is characterized as one that is planted, flowers and sets seed in the same growing season. A winter growth habit line (or "biennial") is characterized as being planted in one season and setting seed in the next growing season. One of ordinary skill will appreciate that flowering time will vary depending upon environmental conditions, but, for example, suitable spring-type lines will flower before July when grown in southern Wisconsin. For hybrid seed production, it is understood that parents should overlap in flowering time. Because of the differences inherent in different environments, it is not possible to predict in advance which lines will be best suited. One skilled in this art, guided by experience in breeding oilseed *B. napus*, understands such variability and appreciates that a line that works well in one geographic position may not work well in another. Although a line must retain the spring growth habit for use in the method, it is not necessary to include the spring marker allele linked to any of the three above-noted vernalization-responsive flowering time loci (See, Examples, infra). It is, however, preferred that the marker alleles be retained for ease of selection.

Suitable hybrids can be produced with this method using existing breeding technology, which can include self-incompatibility (SI) of the female parent (Zeneca), cytoplasmic male sterility (INRA, France), or a system based upon genetic engineering to prevent self pollination (Plant Genetic Systems). The method used by the inventor was the SI system, although this system can break down under high temperatures. This breakdown can be overcome by growth in cool environments, such as is found in Wisconsin near Lake Michigan.

It is anticipated that one or a small number of yield-increasing genes from winter germplasm will be located using the methods described herein. If more than one important gene is found, it is specifically envisioned that the genes can be obtained from populations of several lines of winter oilseed *B. napus*. These genes may be further bred into a hybrid of the type described herein to obtain even higher yields than have been observed to date. Such breeding is expected to be performed using classical breeding in combination with molecular analysis.

Although production of hybrid canola-quality oilseed rape is a desirable result of the method, the method may be equally applied to any oilseed rape. Along these lines, the invention also encompasses a method for producing oil from a hybrid oilseed rape, as well as an oil obtained from seed of a hybrid oilseed rape (including, but not limited to, a canola-quality oilseed rape) produced according to the method of the present invention. Suitable methods for obtaining oil from seed are known. The qualities required in an oil or plant for consumption by animals, including humans, can be independently bred into the plants produced in the present invention. The erucic acid and aliphatic glucosinolate attributes can be selected for either by the physical property or by using genetic markers tightly linked to the genes responsible for ensuring such attributes.

The first approach for producing the spring oilseed rape with winter germplasm introgression utilizes microspore-cultured, doubled haploid (DH) lines from (winter×spring) $F_1$ hybrids, which can be made as described in Ferreira, M. E., et al., RFLP Mapping of *Brassica napus* Using Doubled Haploid Lines,"*Theor. Appl. Genet.* 89:615–621 (1994), incorporated herein by reference, which also describes how to perform an RFLP analysis on genetic material from seedling leaves and how to prepare an RFLP map of the *B. napus* genome. Suitable DH lines for use in the present method can be selected from a collection of such lines on the basis of having a spring growth habit. It is noted that other more complex genetic methods for producing homozygous lines from hybrids exist, although such methods are much less preferred.

Using known restriction fragment length polymorphisms (RFLP), also described by Ferreira, et al. (1994), or other types of molecular markers, one can also monitor the percentage of marker loci in each line that contain an allele that derives from the winter parent, which provides a rough estimate of the percentage of winter germplasm introgression into the spring germplasm. One skilled in the art will appreciate that the precision of this measurement will increase as the number of characterized markers increases and as the marker distribution becomes fully representative of the entire genome.

The doubled haploid lines, which are completely homozygous, can be tested in test crosses against spring-type tester lines that represent a range of genetic diversity. The tester should be a proven good tester in the geographic region in which the plants are to be grown. It is preferred that several spring-type tester lines with different genetic backgrounds be used. It is more preferred that testers from different heterotic groups be used. It is not essential that tester derive from a different heterotic group than the spring parent of the (winter×spring) F1 hybrid. Although such a cross might be expected to yield more, in practice that result is not necessarily observed.

One having ordinary skill possesses certain information about the heterotic grouping of various lines in particular groups. Heterotic groups in oilseed *B. napus* are not as fully defined as they are in other crops such as corn. However, it is known, for example, that hybrids derived from intercrossing lines of different pedigrees and countries of origin (e.g., Canadian, European or Australian) tend to have higher seed yields than hybrids derived from intercrossing lines of the same pedigree and origin. Diers and Osborn (1994), supra, analyzed *B. napus* germplasm using RFLP markers and observed molecular genetic diversity that was generally consistent with known pedigrees. Diers and Osborn (1994), supra, provide guidance on the relatedness of various lines.

The inventors have shown that when a suitable spring line is test crossed with a line having a spring growth habit and any amount of winter germplasm, the resulting hybrid plants, on average, yield higher than open pollinated lines and higher than true (spring×spring) hybrids. It is notable that some of the resulting hybrids can yield more than open pollinated and cultivar lines that were bred specifically for high seed yield (e.g., Hyola 401). It is striking and statistically significant that such high yields were observed in so many individual crosses even though only relatively few (approximately 20) crosses were examined.

It is particularly envisioned that upon analysis of further breedings, segregation of particular winter alleles at particular loci will also correlate strongly with improved yield, and that, ultimately, particular genes encoding such traits will be identified.

A second method for obtaining an oilseed *B. napus* that has the growth habit of a spring line, but which contains germplasm derived from a winter line, is to perform a (winter×spring) cross followed by at least one backcross to the winter parent with selection for spring growth habit. If one or more of the noted vfn-linked RFLP markers are present in the cross, those containing the desired spring growth habit can be efficiently selected at the heterozygous state, which insures segregation of spring types after subsequent selfing. The selected progeny of each backcross can be microspore cultured and colchicine doubled, or selfed, at least one time, to improve homozygosity. Those skilled in the art will understand the predictable genetic effects on the resulting lines from additional backcrossing (introduction of additional winter germplasm) and from additional selfing (greater homozygosity). The resulting lines can be tested as described herein to identify lines with potential for increased yield. It is also possible to perform this analysis using various winter lines, in an effort to identify different winter-type loci that can contribute to higher yield potential.

A third method for broadening the spring germplasm to increase seed yield of hybrid lines by sexual hybridization with winter germplasm involves backcrossing a (winter× spring) $F_1$ hybrid for one or more generations to the spring parent, followed by selfing or microspore culture with colchicine doubling to fix the genetic stock, followed by selection for the spring growth habit. Molecular markers linked to genes that control the spring growth habit can be used for selection, if desired. This method can also be used to characterize and isolate genomic regions of particular interest in improving heterosis.

These methods will be more fully understood upon consideration of the following examples which are intended to be exemplary of the invention but not limiting thereon.

EXAMPLES

Example 1

Nineteen $F_1$-derived doubled haploid lines were selected from the (Major [winter]×Stellar [spring]) cross described by Ferreira, et al. (1994), previously incorporated herein by reference, and by the papers described therein. Major is a European winter cultivar. Stellar is a Canadian spring cultivar. The DH lines were selected from the Ferreira collection on the basis of having an early (spring) flowering habit. The selected lines were then analyzed to determine the percentage of RFLP marker loci having a winter, as opposed to a spring, allele. The DH line having the smallest percentage of winter alleles contained 23% winter alleles. The DH line having the highest percentage of winter alleles contained 73% winter alleles. In this analysis, a total of about 200 RFLP loci were analyzed. Ferreira, et al. (1994) reported 132 RFLP loci. Thormann, et al., *Theor. Appl. Genet.* 93:282–286 (1996), incorporated herein by reference, described a more complete RFLP map. Also, all but two of these DH lines also contained the spring allele at the main flowering locus vfn1, as is shown in Table 1.

in each test. In the tests, both the conventional cultivars and the commercial and non-commercial spring hybrids had lower yields than many of the (DH lines by spring) hybrids. Yields were lower, in general, during the first two tests, although this may be explained in part by high heat that

TABLE 1

Allele at vfn1 and percentage of markers with the winter parent alleles for the selected lines. S = spring allele, W = winter allele.

| | Mef | Mef | Mef | Mef | Mef | Mef | Mef | Mef | Mef | Mef | Mef | Mef | Mef | Mef | Mef | Mef | Mef | Mef | Mef |
|---|---|---|---|---|---|---|---|---|---|---|---|---|---|---|---|---|---|---|---|
| Dh line number | 229 | 140 | 146 | 231 | 136 | 228 | 184 | 112 | 209 | 186 | 237 | 197 | 160 | 191 | 107 | 174 | 216 | 189 | 137 |
| Allele at marker linked to vfn1 | S | S | S | S | S | S | S | S | S | S | S | S | S | S | S | S | S | W | W |
| Percentage of marker loci having winter allele | 23 | 27 | 31 | 37 | 39 | 39 | 42 | 42 | 42 | 43 | 44 | 45 | 48 | 50 | 51 | 58 | 59 | 67 | 73 |

These DH lines were test crossed separately to two genetically distant spring cultivar testers, namely Westar, a spring Canadian canola, and Marnoo, a spring Australian canola. Test crosses were performed in a greenhouse by hand emasculation and controlled pollination. The hybrids thus formed were not necessarily of canola quality, since Major, the source of the winter germplasm, is rapeseed quality.

The hybrids were tested three times for seed yield and other traits, in successive growing seasons. In most of the hybrids produced in the first test, the female parent was the DH line and the tester was the male parent. Seven plants of each tester were used. At least two tester plants were used as female when reciprocal crosses were made. No difference was observed between the reciprocal crosses tested. In subsequent work, the testers, which are commercial cultivars, were the female parent, since they gave better seed sets in the greenhouse. Seeds were kept in cold storage.

The experimental design was a randomized complete block design. The plots were four rows wide, 0.3 meters between rows, and varied in length from 3.6 meters to 4.5 meters in different tests. The center 3.6 meters of the two middle rows were harvested. In the first test, two outer rows were planted with certified Westar seeds. In the second and third tests, the two outer two innetained the same genetic material as the two inner rows, to eliminate upward bias favoring (DH lines×spring) hybrids that could result from greater aggressivity of the hybrids in comparison to adjacent inbreds. The seeding rate was 30 seeds per meter. Trifluralin (2.3 liters of Treflan per ha) was incorporated before seeding. Nitrogen (100 kilograms per ha) was broadcast three weeks after seeding in the first test, and 30 kilograms per ha were applied the same way in the second test. In the third test, the nitrogen was incorporated before seeding. Irrigation was provided in the first two years only to overcome the most severe drought stress (typically, once or twice each year). Hand weeding and pesticide applications were done when necessary. For each plot, the date when half of the plants had at least one open flower was recorded. When seeds started to turn color, the plot was hand harvested, stored in cotton bags and dried at 55° C. and then threshed. Seed weight was taken after samples were left in a dryer at 60° C. for four days to standardize moisture at a low level.

Tables 2, 3, and 4 detail the day of 50% flowering and the mean yield of each parent (Table 2 only), tester, and hybrid in each test. In the tests, both the conventional cultivars and the commercial and non-commercial spring hybrids had lower yields than many of the (DH lines by spring) hybrids. Yields were lower, in general, during the first two tests, although this may be explained in part by high heat that occurred at flowering in both years. Heat avoidance by late flowering alone cannot account for the superiority observed for the DH lines by spring hybrid, as some of the hybrids flowered at the same time as the open pollinated lines and the spring hybrids, yet evidenced greater yields. On average, the yields are comparable to, or better than, commercial lines. Some specific hybrids are much better than commercial hybrids. This result was particularly unexpected because only a few were tested. For example, line 216 was consistently better than Hyola 401. It is thought that the (DH line×spring) hybrids may withstand heat stress better than either the open pollinated lines or the spring hybrids.

Tables 5 (first test), 6 (second test), and 7 (third test), and the corresponding ANOVA tables, show the tendency of the (DH line×spring) hybrids to outyield the others in the three tests. Although Marnoo was a better tester than Westar in the first test, the situation was reversed in the second test. This may have been a result of the tendency of Marnoo hybrids to flower later than their Westar counterparts.

Figure 2:
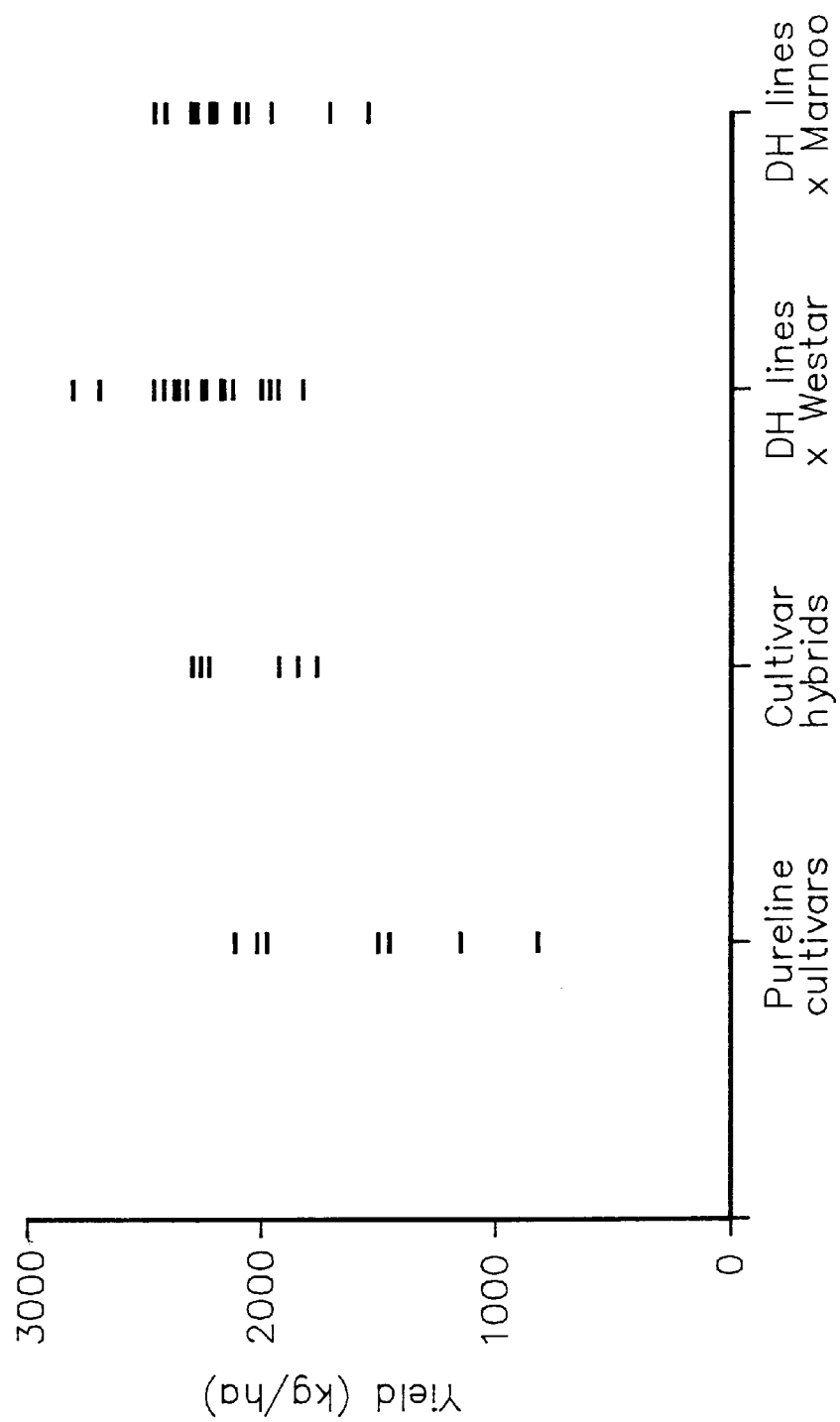
FIG. 2 shows the average yields of the entries in the second test, categorized by type of germplasm.
Figure 3:
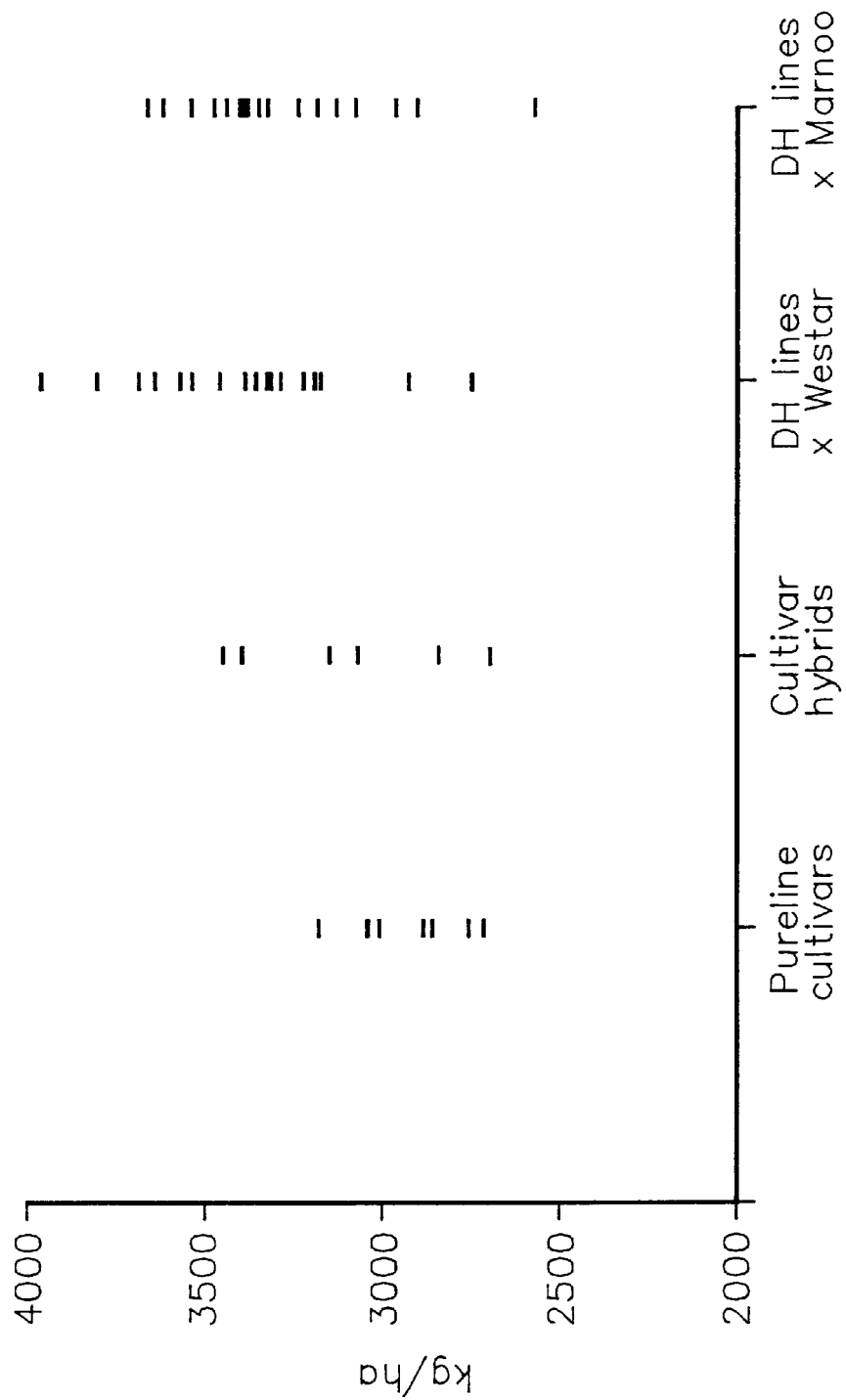
FIG. 3 shows the average yields of the entries in the third test, categorized by type of germplasm.

FIGS. 1–3 show the performance of individual lines in the first, second, and third tests, respectively. It is noted that in each test the tendency in the data is for the (dh×spring) hybrids containing winter germplasm introgression to be higher than the other tested lines.

Correlations between yield, time to flower, and percentage of markers having winter alleles in the parental DH line were also analyzed. In the first test, a positive correlation was observed between percentage of winter alleles and yield for hybrids with either tester. A positive correlation between time to flower and yield occurred only when Marnoo was the tester. In the second test, a negative correlation was observed between percentage of winter alleles and yield, which may have been due to the greater damage caused by a second heat wave on later flowering material. Later flowering plants tended to have higher percentages of winter alleles. Averaged over the first two tests, a positive, although low, association between percentage of winter alleles in the DH line and yield of the hybrid was observed.

TABLE 2

| Entry (First Test) | Day of 50% flowering (after 05/3) | Mean yield (kg/ha) |
| --- | --- | --- |
| Mef 189 | no flower | 0 |
| Mef 186 | 63 | 8 |
| Mef 231 | 65 | 17 |
| Mef 197 | 60 | 112 |
| Mef 237 | 59 | 173 |
| Mef 160 | 44 | 203 |
| Mef 229 | 52 | 210 |
| Mef 104 | 62 | 241 |
| Mef 146 | 50 | 332 |
| Westar self | 47 | 340 |
| Westar certified | 46 | 344 |
| Mef 146 × Westar | 50 | 344 |
| Mef 228 | 70 | 374 |
| Mef 174 | 66 | 391 |
| Mef 191 | 63 | 391 |
| Major × Marnoo | 75 | 436 |
| Stellar self | 49 | 453 |
| Mef 136 | 66 | 473 |
| Marnoo self | 49 | 479 |
| Mef 140 | 59 | 407 |
| Karat | 54 | 564 |
| Mef 112 | 56 | 635 |
| Westar × Marnoo | 48 | 642 |
| Mef 146 × Marnoo | 51 | 691 |
| Marnoo × Mef 160 | 46 | 720 |
| Westar × Mef 231 | 55 | 743 |
| Mef 107 | 69 | 816 |
| Westar × Stellar | 47 | 912 |
| Mef 209 | 68 | 1067 |
| Major × Westar | 71 | 1086 |
| Mef 140 × Westar | 51 | 1157 |
| Mef 229 × Marnoo | 50 | 1157 |
| Mef 189 × Westar | 60 | 1164 |
| Mef 186 × Marnoo | 54 | 1202 |
| Stellar × Marnoo | 50 | 1224 |
| Mef 112 × Marnoo | 52 | 1231 |
| Mef 216 | 61 | 1244 |
| Karat × Westar | 48 | 1255 |
| Karat × Marnoo | 50 | 1263 |
| Mef 209 × Westar | 56 | 1277 |
| Mef 186 × Westar | 52 | 1382 |
| Westar × Mef 160 | 45 | 1397 |
| Mef 228 × Westar | 56 | 1399 |
| Mef 229 × Westar | 49 | 1431 |
| Mef 237 × Westar | 52 | 1508 |
| Mef 237 × Marnoo | 55 | 1545 |
| Mef 191 × Westar | 54 | 1597 |
| Mef 174 x. Westar | 56 | 1615 |
| Mef 104 × Westar | 50 | 1627 |
| Mef 104 × Marnoo | 53 | 1681 |
| Mef 107 × Westar | 58 | 1708 |
| Mef 112 × Westar | 50 | 1710 |
| Westar × Mef 107 | 57 | 1717 |
| Mef 174 × Marnoo | 57 | 1745 |
| Mef 140 × Marnoo | 54 | 1746 |
| Mef 209 × Marnoo | 58 | 1799 |
| Mef 228 × Marnoo | 57 | 1836 |
| Marnoo × Mef 231 | 57 | 1844 |
| Westar × Mef 197 | 50 | 1892 |
| Westar × Mef 136 | 55 | 1936 |
| Mef 216 × Marnoo | 54 | 1966 |
| Mef 191 × Marnoo | 55 | 1980 |
| Marnoo × Mef 136 | 58 | 2086 |
| Marnoo × Mef 107 | 60 | 2223 |
| Mef 216 × Westar | 52 | 2391 |
| Mef 107 × Marnoo | 60 | 2406 |
| Mef 189 × Marnoo | 63 | 2522 |
| Marnoo × 197 | 52 | 2641 |

TABLE 3

| Entry (Second Test) | Day of 50% flowering (after 05/2) | Mean yield (kg/ha) |
| --- | --- | --- |
| Westar certified | 50 | 825 |
| Major × Marnoo | 77 | 1118 |
| Stellar self | 53 | 1163 |
| Westar self | 49 | 1461 |
| Cyclone | 48 | 1503 |
| Marnoo × Mef 189 | 67 | 1558 |
| Marnoo × Mef 160 | 48 | 1730 |
| Major × Westar | 71 | 1750 |
| Marnoo × Stellar | 50 | 1768 |
| Karat × Marnoo | 50 | 1843 |
| Westar × Mef 191 | 55 | 1844 |
| Hyola 401 | 46 | 1916 |
| Westar × Mef 160 | 48 | 1938 |
| Westar × Mef 137 | 59 | 1980 |
| Marnoo × Mef 107 | 58 | 1994 |
| Marnoo × Mef 136 | 59 | 1996 |
| Marnoo × Mef 209 | 59 | 1998 |
| Marnoo self | 50 | 2006 |
| Westar × Mef 140 | 53 | 2036 |
| Crusher | 51 | 2062 |
| Marnoo × Mef 146 | 56 | 2088 |
| Westar × Mef 189 | 62 | 2145 |
| Marnoo × Mef 104 | 50 | 2147 |
| Karat | 54 | 2148 |
| Marnoo × Mef 186 | 54 | 2153 |
| Westar × Mef 231 | 56 | 2194 |
| Westar × Mef 107 | 57 | 2213 |
| Marnoo × Mef 174 | 58 | 2228 |
| Marnoo × Mef 191 | 54 | 2232 |
| Westar × Stellar | 49 | 2236 |
| Marnoo × Mef 231 | 57 | 2248 |
| Marnoo × Mef 216 | 54 | 2252 |
| Westar × Mef 237 | 54 | 2266 |
| Karat × Westar | 50 | 2275 |
| Marnoo × Mef 137 | 63 | 2289 |
| Westar × Mef 186 | 52 | 2293 |
| Marnoo × Westar | 50 | 2308 |
| Marnoo × Mef 237 | 55 | 2313 |
| Marnoo × Mef 197 | 55 | 2345 |
| Westar × Mef 136 | 55 | 2363 |
| Westar × Mef 209 | 57 | 2366 |
| Westar × Mef 229 | 52 | 2374 |
| Westar × Mef 104 | 54 | 2416 |
| Westar × Mef 216 | 52 | 2425 |
| Marnoo × Mef 140 | 53 | 2438 |
| Westar × Mef 174 | 55 | 2447 |
| Marnoo × Mef 229 | 52 | 2448 |
| Westar × Mef 146 | 52 | 2484 |
| Marnoo × Mef 112 | 54 | 2490 |
| Marnoo × Mef 228 | 59 | 2512 |
| Westar × Mef 112 | 52 | 2528 |
| Westar × Mef 228 | 54 | 2703 |
| Westar × Mef 197 | 51 | 2860 |

TABLE 4

| Entry (Third Test) | Day of 50% flowering (after 05/2) | Mean yield (kg/ha) |
| --- | --- | --- |
| Major × Marnoo | 65 | 2714 |
| Westar × Stellar | 51 | 2882 |
| Stellar dh self | 56 | 2897 |
| Westar × Mef 229 | 51 | 2951 |
| Marnoo self | 52 | 2951 |
| Karat × Marnoo | 51 | 3061 |
| Cyclone | 51 | 3081 |
| Westar Self | 50 | 3100 |
| Marnoo × Mef 174 | 58 | 3152 |
| Westar × Mef 160 | 48 | 3184 |
| Marnoo × Mef 160 | 50 | 3206 |
| Westar Certified | 50 | 3264 |
| Karat self | 55 | 3309 |
| Westar × Marnoo | 50 | 3355 |

TABLE 4-continued

| Entry (Third Test) | Day of 50% flowering (after 05/2) | Mean yield (kg/ha) |
|---|---|---|
| Marnoo × Mef 189 | 61 | 3361 |
| Marnoo × Mef 237 | 56 | 3362 |
| Marnoo × Stellar | 52 | 3362 |
| Marnoo × Mef 191 | 56 | 3418 |
| Hyola 401 | 45 | 3455 |
| Crusher | 51 | 3481 |
| Westar × Mef 209 | 60 | 3490 |
| Marnoo × Mef 229 | 53 | 3498 |
| Westar × Mef 231 | 57 | 3505 |
| Westar × Mef 174 | 57 | 3506 |
| Westar × Mef 186 | 55 | 3543 |
| Marnoo × Mef 186 | 58 | 3561 |
| Westar × Mef 197 | 56 | 3624 |
| Westar × Mef 237 | 55 | 3653 |
| Westar × Mef 191 | 57 | 3658 |
| Westar × Mef 228 | 56 | 3668 |
| Marnoo × Mef 228 | 58 | 3670 |
| Marnoo × Mef 112 | 54 | 3691 |
| Westar × Mef 146 | 55 | 3709 |
| Marnoo × Mef 140 | 55 | 3734 |
| Marnoo × Mef 231 | 58 | 3747 |
| Marnoo × Mef 104 | 53 | 3751 |
| Major × Westar | 64 | 3753 |
| Marnoo × Mef 137 | 60 | 3762 |
| Marnoo × Westar | 50 | 3775 |
| Marnoo × Mef 197 | 53 | 3817 |
| Westar × Mef 189 | 60 | 3831 |
| Karat × Westar | 51 | 3832 |
| Marnoo × Mef 136 | 57 | 3860 |
| Marnoo × Mef 209 | 59 | 3935 |
| Marnoo × Mef 107 | 57 | 3941 |
| Westar × Mef 104 | 55 | 3944 |
| Westar × Mef 140 | 53 | 3986 |
| Marnoo × Mef 216 | 57 | 4044 |
| Westar × Mef 107 | 57 | 4074 |
| Marnoo × Mef 146 | 57 | 4097 |
| Westar × Mef 112 | 53 | 4145 |
| Westar × Mef 137 | 59 | 4265 |
| Westar × Mef 136 | 56 | 4275 |
| Westar × Mef 216 | 55 | 4482 |

TABLE 5

Summary and ANOVA table of data from first test

| Groups | Count | Average Yield (kg/ha) | Standard deviation |
|---|---|---|---|
| OP and inbreds | 5 | 436 | 95 |
| Spring hybrids | 5 | 1059 | 275 |
| Dh lines × Westar | 19 | 1473 | 443 |
| Dh lines × Marnoo | 19 | 1738 | 549 |

| Source of Variation | SS | df | MS | F | P-value |
|---|---|---|---|---|---|
| Between Groups | 7466295. | 3 | 2488765. | 11.8 | $8.514 \times 10^{-6}$ |
| Within Groups | 9287658. | 44 | 211083. | | |
| Total | 16753953. | 47 | | | |

TABLE 6

Summary and ANOVA table of data from second test

| Groups | Count | Average Yield (kg/ha) | Standard deviation |
|---|---|---|---|
| OP and inbreds | 7 | 1596 | 500 |
| Spring hybrids | 6 | 2058 | 241 |
| Dh lines × Westar | 19 | 2309 | 256 |
| Dh lines × Marnoo | 19 | 2182 | 249 |

| Source of Variation | SS | df | MS | F | P-value |
|---|---|---|---|---|---|
| Between Groups | 2691762. | 3 | 897254. | 10.3 | $2.474 \times 10^{-5}$ |
| Within Groups | 4087282. | 47 | 86963. | | |
| Total | 6779044 | 50 | | | |

TABLE 7

Summary and ANOVA table of data from third test

| Groups | Count | Average yield (kg/ha) | Standard deviation |
|---|---|---|---|
| OP and inbreds | 7 | 3155 | 208 |
| Spring hybrids | 7 | 3389 | 345 |
| Dh lines × Westar | 19 | 3763 | 385 |
| Dh lines × Marnoo | 19 | 3663 | 272 |

| Source of Variation | SS | df | MS | F | P-Value |
|---|---|---|---|---|---|
| Between Groups | 2276369 | 3 | 758790 | 7.3 | 0.000384 |
| Within Groups | 4967765 | 48 | 103495 | | |
| Total | 7244134 | 51 | | | |

Example 2

Two winter canola-quality cultivars were converted to spring growth habit by crossing a winter cultivar (either Ceres [German] or Samourai [French]) with a spring canola-quality cultivar (Westar [Canadian]). The $F_1$ hybrid of each such cross was backcrossed twice to the winter cultivar parent (although one backcross may be sufficient). Each backcross was screened with RFLP marker probes to obtain plants heterozygotic (spring/winter) at marker loci linked to vfn1 and vfn2. WG6B10, is a suitable RFLP locus for distinguishing spring and winter alleles of vfn1. The RFLP alleles detected by WG6B10, for an EcoRI digest, are 20 kb in Westar (and most Canadian spring cultivars) and 11 kb for Samourai and Ceres (and most European winter cultivars). WG7B3, is a suitable RFLP locus for distinguishing spring and winter alleles of vfn2. The RFLP alleles detected by WG7B3, for an HindIII digest, are 2 kb in Westar and 3.3 kb for Samourai. The allele in Ceres is the same as in Westar, so it is not used for selection in the backcross of Westar to Ceres. WG7B3 can be used for selection if it is variant between the lines being crossed. It may not be variant between some of the spring and winter lines that one can choose. It may be sufficient to use markers linked to any one vfn locus, or two or three vfn loci could be used. Other markers linked to these genes can also be obtained using standard RFLP analysis methods.

These loci may also serve as the basis for a PCR probing strategy to distinguish the winter and spring alleles. The terminal sequences of a clone at the WG6B10 locus are shown in SEQ ID NO:1 and SEQ ID NO: 2. The terminal sequences of a clone at the WG7B3 locus are shown in SEQ ID NO:3 and SEQ ID NO: 4. These sequences include PCR primer binding sites (identified in the Sequence Listing) and it is believed by the inventors that a suitable PCR probing strategy may be developed using these primers. First backcrosses were also analyzed with about 20 marker loci chosen at random from outside the vfn1 and vfn2 regions to select for homozygous winter germplasm at those loci, thus increasing the winter nature of the background germplasm. Second backcrosses were screened with about 20 additional markers.

After one round of backcrossing, the first backcross was self-pollinated twice. After two rounds of backcrossing, the second round was self-pollinated once. Note that it would also be possible to employ the microspore culture method here to obtain homozygous doubled haploid lines.

The estimated percentage of winter and spring alleles in the germplasm in various lines is shown in Table 8. The selfed progeny of the second backcross contained about 85% fixed winter markers (by RFLP) and do include the spring alleles for markers linked to the vfn1 and vfn2 spring growth habit genes. Yield data for these test crosses is shown in Table 9. In Table 9, BC_ identifies the backcross, (S) or (C) identifies the winter cultivar that was backcrossed (Samourai or Ceres), S_ identifies the selfing generation, and A, B, and C identify selected plants.

TABLE 8

Characteristics of spring-type lines with winter germplasm introgression

| Recurrent parent[a] | Donor parent | Generation | No. of lines | % fixed[b] W | % fixed[b] S | No. of marker regions[c] |
|---|---|---|---|---|---|---|
| Ceres (W) | Westar (S) | BC1S2 | 2 | 58 | 25 | 18 |
| Samourai (W) | Westar (S) | BC1S2 | 3 | 68 | 11 | 19 |
|  |  | BC2S1 | 2 | 82–83 | 2 | 36–37 |

[a]W = winter-type, S = spring-type parent
[b]% of genome homozygous for winter (W) alleles and spring (S) alleles (remainder is segregating) estimated from marker data (marker/phenotype selected lines) or predicted average for population based on theory (unselected lines)
[c]Number of unlinked marker loci analyzed, tbd = to be determined The progeny of these crosses were test crossed with Marnoo [Australian], Westar [Canadian] or Topas [European] self-incompatible spring testers. The resulting $F_1$ hybrids were tested two times for seed yield and other traits, in successive growing years. The tests also included $F_1$ hybrids from crosses among the three testers and commercial $F_1$ hybrids (Hyola 401 and Hyola 420). The first test was conducted as described for Example 1; the second test was conducted in the same way except plots were spaced one foot apart with seven rows six inches apart and eight feet long; six feet of the seven rows were harvested for seed. Tables 9 (first test) and 10 (second test) detail the mean yield of each hybrid. In the first test, over one-half of the hybrids with winter germplasm yielded more than all of the spring× spring hybrids, and the best hybrid with winter germplasm yielded 335% more than the best spring×spring hybrid.

TABLE 9

| Entry (first year) | Average Yield (kg/ha) |
|---|---|
| Marnoo × BC2(S)S1B | 2373 |
| Marnoo × BC1(S)S2B | 2521 |
| Westar × BC1(S)S2B | 2682 |
| Topas × BC1(C)S2A | 2704 |
| Westar × BC1(C)S2B | 2709 |
| Hyola 420 | 2758 |
| Marnoo × BC1(S)S2C | 2790 |
| Topas × Marnoo | 2794 |
| Westar × Marnoo | 2808 |
| Hyola 401 | 2911 |
| Topas × Westar | 2929 |
| Marnoo × BC1(S)S2A | 2947 |
| Topas × BC1(S)S2C | 3014 |
| Westar × BC1(C)S2A | 3050 |
| Topas × BC2(S)S1B | 3063 |
| Westar × BC1(S)S2A | 3077 |
| Topas × BC1(S)S2A | 3113 |
| Marnoo × BC1(C)S2B | 3117 |
| Topas × BC1(C)S2B | 3202 |
| Marnoo × BC1(C)S2A | 3211 |
| Westar × BC1(S)S2C | 3283 |
| Topas × BC1(S)S2B | 3458 |
| Marnoo × BC2(S)S1A | 3624 |
| Westar × BC2(S)S1B | 3911 |

In the second test, over one-quarter of the hybrids with winter germplasm yielded more than all of the (spring× spring) hybrids, and the best hybrid with winter germplasm yielded 29% more than the best (spring×spring) hybrid. The best hybrid from the first test was included at one location in the Wisconsin Spring Canola Cultivar Trial in the following year, and it had the highest yield of all entries, including both open pollinated cultivars and (spring×spring) hybrids.

TABLE 10

| Entry (first year) | Average Yield (kg/ha) |
|---|---|
| Westar × BC1(S)S2B | 1293 |
| Westar × BC1(S)S2C | 1338 |
| Topas × Westar | 1478 |
| Marnoo × BC2(S)S1B | 1479 |
| Topas × BC1(C)S2B | 1573 |
| Topas × BC1(S)S2B | 1597 |
| Hyola 401 | 1604 |
| Westar × BC2(S)S1B | 1664 |
| Marnoo × BC1(S)S2C | 1801 |
| Marnoo × BC1(S)S2A | 1846 |
| Westar × BC1(S)S2A | 1866 |
| Marnoo × BC1(C)S2B | 1871 |
| Topas × BC1(S)S2C | 1883 |
| Marnoo × BC2(S)S1A | 1902 |
| Topas × Marnoo | 1922 |
| Westar × BC1(C)S2A | 1925 |
| Westar × BC2(S)S1A | 2084 |
| Marnoo × BC1(S)S2B | 2105 |
| Westar × Marnoo | 2114 |
| Topas × BC1(S)S2A | 2114 |
| Marnoo × BC1(C)S2A | 2141 |
| Westar × BC1(C)S2B | 2143 |
| Topas × BC2(S)S1A | 2213 |
| Topas × BC1(C)S2A | 2319 |
| Topas × BC2(S)S1B | 2730 |

Example 3

A winter cultivar (Ceres [German]) and a spring cultivar (either Westar [Canadian] or Marnoo [Australian]) were crossed and the $F_1$ hybrid progeny were backcrossed without selection to the spring parent twice. After the first backcross, the backcross population was self-pollinated three times before being tested. After the second backcross, the backcross was self-pollinated two times before being tested. The estimated percentage of homozygous winter and spring germplasm present in each population is shown in Table 11. The self-pollinated progeny of the first backcross contained about 25% winter genes, while the progeny of the second backcross contained about 12.5% winter alleles at marker loci.

TABLE 11

Characteristics of spring-type lines with winter germplasm introgression

| Recurrent parent[a] | Donor parent | Generation | No. of lines | % fixed[b] W | S |
|---|---|---|---|---|---|
| Westar (S) | Ceres (W) | BC1S3 | 60 | 21.88 | 71.88 |
|  |  | BC1S2 | 60 | 9.38 | 84.38 |
| Marnoo (S) | Ceres (W) | BC1S3 | 60 | 21.88 | 71.88 |
|  |  | BC2S2 | 60 | 9.38 | 84.38 |

[a]W = winter-type, S = spring-type parent
[b]average % of genome homozygous for winter (W) alleles and spring (S) alleles (remainder is segregating) predicted for generations based on theory The BC1S3 and BC1S2 lines were test crossed with a self-incompatible tester (Topas [European]) and about 60 hybrids of each population were tested one time for seed yield and other traits. The test was conducted as described for Example 1. Table 12 details the average yield for the hybrids from each population and the yields for the hybrids from each population and the yields for spring open-pollinated and inbreds and spring hybrids that were included in the test. The average of all hybrids for each population with winter germplasm was not higher than the average yield of the spring×spring hybrids. This is not unexpected because each line had only a small portion of the winter germplasm and no selection for yield was practiced; as is typical before releasing a cultivar. However, the average yield of the best 25% of the hybrids from each population was higher than the average yield of the spring×spring hybrids.

From each of the four populations, three of the highest yielding in the first test were selected to be included in the Wisconsin Spring Canola Cultivar Trial the following year. The three hybrids were replicated across three locations. Due to low seed availability, individual hybrids were not replicated within each location, as were the other entries (four replicates per location), but the three hybrids from each population were considered as replicates for the population at a location. Table 12 shows the results of this test. Hybrids from the two populations containing winter germplasm and derived by two rounds of backcrossing were higher yielding than all other spring OP and hybrid entries.

TABLE 12

| Entry | Number of plots | Average yield (kg/ha) |
|---|---|---|
| Cyclone (spring OP) | 12 | 1596 |
| Hudson (spring OP) | 12 | 1615 |
| Hyola 401 (spring hybrid) | 12 | 1632 |
| Crusher (spring OP) | 12 | 1771 |
| BNS9043 (OP or hybrid unknown) | 12 | 1773 |
| Three hybrids selected from M_BC1S3 | 9 | 1851 |
| Three hybrids selected from W_BC1S3 | 9 | 1873 |
| GOH12 (OP or hybrid unknown) | 12 | 1969 |
| CL2070 (spring hybrid) | 12 | 2065 |
| Three hybrids selected from W_BC2S2 | 9 | 2190 |
| Three hybrids selected from M_BC2S2 | 9 | 2211 |

The present invention is not intended to be limited to the foregoing embodiments, but rather to encompass all such variations and modifications as come within the scope of the appended claims.

We claim:

1. A method for producing a hybrid oilseed *Brassica napus*, the method comprising the steps of:
   (a) crossing an oilseed *B. napus* line that comprises germplasm derived from at least one winter line but which has a spring growth habit with at least one tester line which has a spring growth habit to produce hybrid plants;
   (b) harvesting seeds from the hybrid plants;
   (c) growing plants from the seeds of step (b);
   (d) harvesting seeds from the plants of step (c);
   (e) evaluating yield of the seeds of step (d); and
   (f) selecting from the hybrid plants of step (b) a hybrid having an average seed yield reproducibly higher in more than one growing season than hybrids derived only from spring lines having no winter germplasm that went into the hybrids of step (a).

2. A method as claimed in claim 1 wherein the selecting step comprises analyzing molecular markers that distinguish between spring germplasm and winter germplasm.

3. A method as claimed in claim 1 wherein the oilseed *B. napus* line of step (a) is an inbred line derived from a (winter×spring) $F_1$ hybrid.

4. A method as claimed in claim 1 wherein step (a) comprises the steps of:
   crossing a winter parent line with a spring parent line to produce (winter×spring) $F_1$ hybrids;
   backcrossing the (winter×spring) $F_1$ hybrids at least once to a winter parent line; and
   selecting for a spring growth habit to obtain backcross progeny comprising germplasm derived from a winter parent line but having a spring growth habit.

5. A method as claimed in claim 4 further comprising the step of inbreeding the backcross progeny.

6. A method as claimed in claim 1 wherein step (a) comprises the steps of:
   crossing a winter parent line and a spring parent line to produce a (winter×spring) $F_1$ hybrid; and
   backcrossing the (winter×spring) $F_1$ hybrid to a spring parent line at least once to obtain backcross progeny comprising germplasm derived from a winter parent line but having a spring growth habit.

7. A method as claimed in claim 6 further comprising the step of inbreeding the backcross progeny.

8. A hybrid oilseed *Brassica napus* prepared according to a method comprising the steps of:
   (a) crossing an oilseed *B. napus* line that comprises germplasm derived from at least one winter line but which has a spring growth habit with at least one tester line which has a spring growth habit to produce hybrid plants;
   (b) harvesting seeds from the hybrid plants;
   (c) growing plants from the seeds of step (b);
   (d) harvesting seeds from the plants of step (c);
   (e) evaluating yield of the seeds of step (d) and
   (f) selecting from the hybrid plants of step (b) a hybrid having an average seed yield reproducibly higher in more than one growing season than hybrids derived only from spring lines having no winter germplasm that went into the hybrids of step (a).

9. A hybrid oilseed *Brassica napus* prepared according to the method as claimed in claim 8 wherein the selecting step of claim 8 comprises the step of:
   analyzing molecular markers that distinguish between spring germplasm and winter germplasm.

10. A hybrid oilseed *Brassica napus* line prepared according to the method as claimed in claim 8 wherein the oilseed *B. napus* of step (a) is an inbred line derived from a (winter×spring) $F_1$ hybrid.

11. A hybrid oilseed *Brassica napus* prepared according to the method as claimed in claim 8 wherein step (a) comprises the steps of:
   crossing a winter parent line with a spring parent line;
   backcrossing the (winter×spring) $F_1$ hybrids at least once to a winter parent line; and
   selecting for a spring growth habit to obtain backcross progeny comprising germplasm derived from a winter parent line but having a spring growth habit.

12. A hybrid oilseed *Brassica napus* prepared according to the method as claimed in claim 11, further comprising the step of inbreeding the backcross progeny.

13. A hybrid oilseed *Brassica napus* prepared according to the method as claimed in claim 8 wherein step (a) comprises the steps of:
   crossing a winter parent line and a spring parent line to produce a (winter×spring) $F_1$ hybrid; and
   backcrossing the (winter×spring) $F_1$ hybrid to a spring parent line at least once to obtain backcross progeny comprising germplasm derived from a winter parent line but having a spring growth habit.

14. A hybrid oilseed *Brassica napus* prepared according to the method as claimed in claim 13, further comprising the step of inbreeding the backcross progeny.

15. A method for producing oil from a hybrid oilseed *Brassica napus*, the method comprising the steps of:
   (a) crossing an oilseed *B. napus* line that comprises germplasm derived from at least one winter line but which has a spring growth habit with at least one tester line which has a spring growth habit to produce hybrid plants;
   (b) harvesting seeds from the hybrid plants;
   (c) growing plants from the seeds of step (b);
   (d) harvesting seeds from the plants of step (c);
   (e) evaluating yield of the seeds of step (d);
   (f) selecting from the hybrid plants of step (b) a hybrid having an average seed yield reproducibly higher in more than one growing season than hybrids derived only from spring lines having no winter germplasm that went into the hybrids of step (a);
   (g) collecting seeds from a selected hybrid; and
   (h) removing oil from the seeds.

16. Seed produced by the hybrid *Brassica napus* plant of claim 8.

17. The method of claim 2, wherein said molecular marker is a vfn-linked molecular marker.

18. The hybrid of claim 9, wherein said molecular marker is a vfn-linked molecular marker.

* * * * *

UNITED STATES PATENT AND TRADEMARK OFFICE
CERTIFICATE OF CORRECTION

PATENT NO. : 6,069,302
DATED : May 30, 2000
INVENTOR(S) : Thomas C. Osborn and David V. Butruille It is certified that error appears in the above-identified patent and that said Letters Patent is hereby corrected as shown below:

Col. 7, Line 47, "two innetained" should read -- rows contained --.

Signed and Sealed this

Tenth Day of April, 2001

Attest:

NICHOLAS P. GODICI

*Attesting Officer*     *Acting Director of the United States Patent and Trademark Office*